(12) United States Patent
Tokumaru et al.

(10) Patent No.: US 7,514,553 B2
(45) Date of Patent: Apr. 7, 2009

(54) PROCESS FOR PRODUCING PENICILLANIC ACID COMPOUND

(75) Inventors: Yoshihisa Tokumaru, Tokushima (JP); Norio Saito, Tokushima (JP); Makoto Akizuki, Tokushima (JP)

(73) Assignees: Otsuka Chemical Co., Ltd., Osaka (JP); Taiho Pharmaceutical Co., Ltd., Tokyo (JP)

( * ) Notice: Subject to any disclaimer, the term of this patent is extended or adjusted under 35 U.S.C. 154(b) by 436 days.

(21) Appl. No.: 10/569,692

(22) PCT Filed: Sep. 2, 2004

(86) PCT No.: PCT/JP2004/013097

§ 371 (c)(1),
(2), (4) Date: Feb. 27, 2006

(87) PCT Pub. No.: WO2005/023821

PCT Pub. Date: Mar. 17, 2005

(65) Prior Publication Data

US 2006/0281917 A1    Dec. 14, 2006

(30) Foreign Application Priority Data

Sep. 3, 2003    (JP) .............................. 2003-311709

(51) Int. Cl.
*C07D 477/06* (2006.01)
(52) U.S. Cl. ..................................... 540/310
(58) Field of Classification Search ................. 540/310
See application file for complete search history.

(56) References Cited

U.S. PATENT DOCUMENTS

| | | | | |
|---|---|---|---|---|
| 4,468,351 A * | 8/1984 | Pirie et al. | ............ | 540/310 |
| 4,588,527 A * | 5/1986 | Pirie et al. | ............ | 540/310 |
| 4,639,335 A * | 1/1987 | Martel et al. | ............ | 540/304 |
| 4,816,580 A * | 3/1989 | Hansen | ............ | 540/310 |
| 6,271,421 B1 * | 8/2001 | King | ............ | 568/316 |

FOREIGN PATENT DOCUMENTS

| | | |
|---|---|---|
| EP | 0 129 360 A1 | 12/1984 |
| EP | 0 139 048 A1 | 5/1985 |
| EP | 0 262 202 B1 | 7/1992 |
| EP | 0 999 213 A1 | 5/2000 |
| EP | 1 041 075 A1 | 10/2000 |
| JP | 60-8293 | 1/1985 |
| JP | 60-120883 | 6/1985 |
| JP | 61-63683 | 4/1986 |
| JP | 63-503072 | 11/1988 |
| JP | 10-245386 | 9/1998 |
| JP | 2000-264889 | 9/2000 |

OTHER PUBLICATIONS

Akhtar et al., Journal of Organic Chemistry (1990), 55(18), 5222-5.*

* cited by examiner

*Primary Examiner*—Mark L Berch
(74) *Attorney, Agent, or Firm*—Wenderoth, Lind & Ponack, L.L.P.

(57) ABSTRACT

A process for preparing a penicillanic acid compound of the formula (2) comprising reacting a halogenated penicillanic acid compound of the formula (1), (a) in the presence of a metal bismuth or bismuth compound, (b) with a metal having a lower standard oxidation-reduction potential than bismuth to obtain the compound (2)

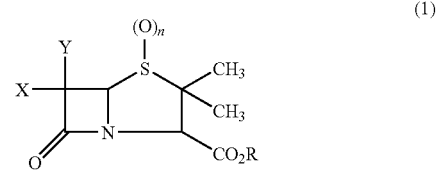

(1)

(X and Y are a hydrogen atom or halogen atom, provided that X and Y are not hydrogen atoms at the same time, n is an integer of 0 to 2, R is carboxylic acid protecting group)

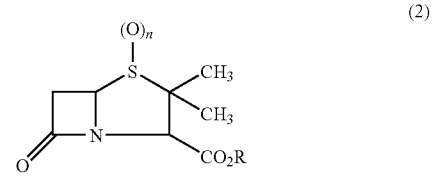

(2)

(n and R are same as above).

11 Claims, No Drawings

PROCESS FOR PRODUCING PENICILLANIC ACID COMPOUND

TECHNICAL FIELD

The present invention relates to a novel process for preparing a penicillanic acid compound. The penicillanic acid compound obtained by the present process is useful, for example, as an intermediate for β-lactamase inhibitor.

BACKGROUND ART

Processes are known for preparing a penicillanic acid compound of the formula (2) from a halogenated penicillanic acid compound of the formula (1), by catalytic reduction with use of a noble metal catalyst, by reaction with organic tin hydride compound, by reaction with zinc, by electrolytic reduction method, by reaction with aluminum and a catalytic amount of metal lead or lead compound (for example, patent literatures 1 to 4, non-patent literatures 1 to 2).

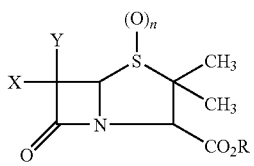
(1)

(X and Y are a hydrogen atom or halogen atom, provided that X and Y are not hydrogen atoms at the same time, n is an integer of 0 to 2, R is carboxyl protecting group)

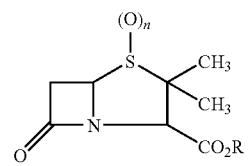
(2)

(n and R are same as above).

[patent literature 1] JP 1980-120588 A
[patent literature 2] JP 1982-169486 A
[patent literature 3] JP 1986-63683 A
[patent literature 4] JP 1989-66189 A
[non-patent literature 1] Nature, 201, 1124 (1964)
[non-patent literature 2] J. Chem. Soc., (C), 2123 (1968)

The catalytic reduction with use of a noble metal catalyst requires a large amount of an expensive noble metal catalyst and demands application of dangerous hydrogen pressure, therefore the method is not practical. The organic tin hydride compound is a reagent which is difficult to be used industrially and the organic tin compound is harmful. The process using zinc affords the desired product which is low in yield and purity. The electrolytic reduction requires special apparatus and has problems for industrial operation. Further, it is considered that the use of lead is preferably restricted from the viewpoint of environmental care.

An object of the invention is to provide a process for preparing a penicillanic acid compound of the formula (2) which is free of industrial problems, safe, simple in procedures and industrially advantageous.

DISCLOSURE OF THE INVENTION

The present invention provides the following processes for preparing a penicillanic acid compound.

1. A process for preparing a penicillanic acid compound of the formula (2) comprising reacting a halogenated penicillanic acid compound of the formula (1), (a) in the presence of a metal bismuth or bismuth compound, (b) with a metal having a lower standard oxidation-reduction potential than bismuth to obtain the compound (2)

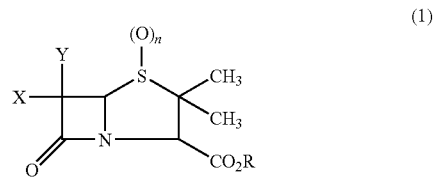
(1)

(X and Y are a hydrogen atom or halogen atom, provided that X and Y are not hydrogen atoms at the same time, n is an integer of 0 to 2, R is carboxylic acid protecting group)

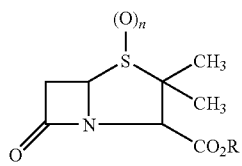
(2)

(n and R are same as above).

2. A process for preparing a penicillanic acid compound of the formula (2) comprising reacting a dihalogenated penicillanic acid compound of the formula (1a), (a) in the presence of a metal bismuth or bismuth compound, (b) with a metal having a lower standard oxidation-reduction potential than bismuth to obtain a monohalogenated penicillanic acid compound of the formula (1b), and reacting the compound (1b) with a metal having a lower standard oxidation-reduction potential than bismuth in the presence of a metal bismuth or bismuth compound to obtain the compound (2)

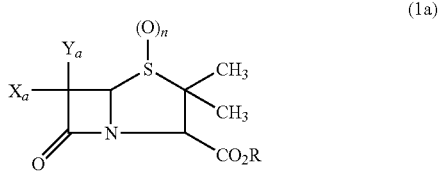
(1a)

(Xa and Ya are a halogen atom, n and R are same as above)

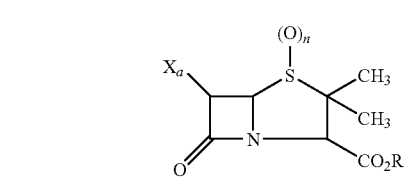

(Xa, n and R are same as above).

3. A process for preparing a monohalogenated penicillanic acid compound of the formula (1b) comprising reacting a dihalogenated penicillanic acid compound of the formula (1a), (a) in the presence of a metal bismuth or bismuth compound, (b) with a metal having a lower standard oxidation-reduction potential than bismuth to obtain the compound (1b).

4. A process for preparing a penicillanic acid compound of the formula (2) comprising reacting a monohalogenated penicillanic acid compound of the formula (1b), (a) in the presence of a metal bismuth or bismuth compound, (b) with a metal having a lower standard oxidation-reduction potential than bismuth to obtain the compound (2).

In the present invention, it is found that a dehalogenated penicillanic acid compound can be obtained, (a) in the presence of a metal bismuth or bismuth compound which is relatively less harmful and less environmental problems, (b) using a metal having a lower standard oxidation-reduction potential than bismuth, and thus the present invention has been accomplished.

In the present invention, it is possible to obtain a dehalogenated penicillanic acid compound in high purity and high yield from 6-halogenated penicillanic acid compound, (a) in the presence of a metal bismuth or bismuth compound, (b) using a metal having a lower standard oxidation-reduction potential than bismuth.

In the present specification, examples of halogen atom are fluorine, chlorine, bromine or iodine atom.

Any known carboxylic acid protecting groups are usable. The groups disclosed in Theodora W. Greene, "Protective Groups in Organic Synthesis", Chap. 5 are widely usable. Preferred examples thereof are benzyl, p-methoxybenzyl, p-nitrobenzyl, diphenylmethyl, trimethoxybenzyl, tert-butyl, methoxyethoxymethyl, piperonyl, ditolylmethyl, trimethoxy-dichlorobenzyl, trichloromethyl and bis(p-methoxyphenyl)methyl.

In the present invention, it is possible to prepare a dehalogenated penicillanic acid compound by reacting a halogenated penicillanic acid compound of the formula (1), in the presence of a metal bismuth or bismuth compound, with a metal having a lower standard oxidation-reduction potential than bismuth.

The reaction is considered to proceed as the following reaction scheme-1.

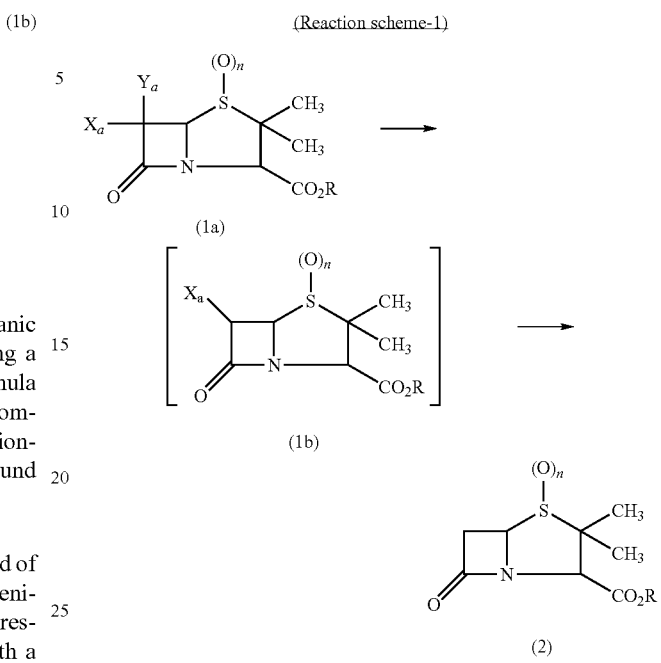

(Xa and Ya are a halogen atom, R is carboxylic acid protecting group, n is an integer of 0 to 2,)

Namely, the penicillanic acid compound of the formula (2) can be prepared from the dihalogenated penicillanic acid compound of the formula (1a) via the monohalogenated penicillanic acid compound of the formula (1b).

In the present process, it is usually possible to lead to the penicillanic acid compound of the formula (2) without isolating the monohalogenated penicillanic acid compound of the formula (1b). However, it is possible to prepare and isolate the monohalogenated penicillanic acid compound of the formula (1b) from the dihalogenated penicillanic acid compound of the formula (1a). The penicillanic acid compound of the formula (2) can be prepared from the isolated monohalogenated penicillanic acid compound of the formula (1b) by the present process.

The reaction conditions in the step of preparing the monohalogenated penicillanic acid compound of the formula (1b) from the dihalogenated penicillanic acid compound of the formula (1a) may be the same as the reaction conditions in the step of preparing the penicillanic acid compound of the formula (2) from the monohalogenated penicillanic acid compound of the formula (1b).

The shape of the metal bismuth can be any of lump, plate, foil, powder or the like but preferably is in the form of a powder which is great in surface area.

Any known bismuth compounds can widely be used. Examples thereof are bismuth halides such as bismuth fluoride, bismuth chloride, bismuth bromide, and bismuth iodied; bismuth salts of mineral acid such as bismuth nitrate and bismuth sulfate; bismuth oxyhalides such as bismuth oxychloride; bismuth salts of aliphatic acid such as bismuth acetate; and bismuth oxide. The bismuth compound may be in the form of hydrate. The metal bismuth and the bismuth compound can be used singly or a mixture of at least one of them, respectively. Among these metal bismuth and bismuth compounds preferable are a bismuth halide and a bismuth salt of mineral acid, particularly preferable are bismuth chloride, bismuth nitrate and bismuth sulfate.

These metal bismuth compounds can be used usually in an amount of about 0.00001 to about 0.5 mole, preferably 0.0001 to 0.2 mole, per mole of the halogen atom of the halogenated penicillanic acid compound of the formula (1), (1a) or (1b) [hereinafter referred to simply as the compound of the formula (1)].

Examples of metals having a lower standard oxidation-reduction potential than that of bismuth are aluminum, iron, magnesium, etc., among which aluminum and iron are desirable and aluminum is particularly desirable to use. The shape of these metals is not limited particularly but can be any of a wide variety of forms such as powder, plate, lump, foil and wire. Preferably, the metal to be used is in the form of a powder in view of proceeding the reaction fluently. The particle size of the powdery metal is preferably about 10 to about 3000 μm although variable over a wide range. These metals are used usually in an amount of about 0.5 to about 50 moles, preferably about 1 to about 5 moles, per mole of the halogenated penicillanic acid compound of the formula (1).

The present reaction is conducted in a suitable solvent. Examples of solvents useful in the reaction are organic solvents, for example, lower alkyl alcohols having 1 to 4 carbon atoms such as methanol, ethanol, propanol, 2-propanol, butanol and tert-butanol; lower alkyl esters of lower carboxylic acids such as methyl formate, ethyl formate, propyl formate, butyl formate, methyl acetate, ethyl acetate, propyl acetate, butyl acetate, methyl propionate and ethyl propionate; ketones such as acetone, methyl ethyl ketone, methyl propyl ketone, methyl butyl ketone, methyl isobutyl ketone and diethyl ketone; ethers such as diethyl ether, ethyl propyl ether, ethyl butyl ether, dipropyl ether, diisopropyl ether, dibutyl ether and dimethoxyethane; cyclic ethers such as tetrahydrofuran and dioxane; nitriles such as acetonitrile, propionitrile, butyronitrile and valeronitrile; substituted or unsubstituted aromatic hydrocarbons such as benzene, toluene, xylene, chlorobenzene and anisole, hydrocarbon halides such as dichloromethane, chloroform, dichloroethane, trichloroethane, dibromoethane, propylene dichloride and carbon tetrachloride; aliphatic hydrocarbons such as pentane, hexane, heptane and octane, cycloalkanes such as cyclopentane, cyclohexane, cycloheptane and cyclooctane, amides such as dimethylformamide and dimethylacetamide, sulfoxides such as dimethylsulfoxide, etc. These organic solvents are used singly or in admixture of at least two of them. These organic solvents are used in an amount of about 1 to about 500 liters, preferably about 2.5 to about 50 liters, per kilogram of the compound of the formula (1), although not limited particularly. Water may be added to the organic solvent as required. Water may be added in an amount of about 0.01 to about 50 liters, preferably about 0.05 to about 30 liters, more preferably about 0.1 to about 10 liters, per kilogram of the compound of the formula (1).

Among these organic solvents preferable is a solvent mixture of a lower aklyl alcohol and an organic solvent other than the alcohol. More preferable is a solvent mixture of a lower aklyl alcohol and a hydrocarbon halide. In the solvent mixture preferable lower aklyl alcohol are methanol, ethanol and 2-propanol, and particularly preferable is methanol. Particularly preferable hydrocarbon halide is dichloromethane. In the solvent mixture, the organic solvent other than the lower aklyl alcohol is used in an amount of 0.3 to 30 volume parts, preferably 0.5 to 20 volume parts, per volume part of the alcohol.

In the present process, a reaction promoter or reaction auxiliary agent is preferably usable. Examples of the promoters or auxiliary agents are alkali metal halides such as lithium fluoride, lithium chloride, lithium bromide, lithium iodide, sodium fluoride, sodium chloride, sodium bromide, sodium iodide, potassium fluoride, potassium chloride, potassium bromide and potassium iodide; alkaline earth metal halides such as magnesium chloride, magnesium bromide and calcium chloride; ammonium halides such as ammonium fluoride, ammonium chloride, ammonium bromide and ammonium iodide; alkyl ammonium salts such as trimethylammonium hydrochloride; mineral acids such as hydrochloric acid, sulfuric acid, nitric acid, hydrobromic acid and phosphoric acid; carboxylic acids such as formic acid, acetic acid, monochloroacetic acid, dichloroacetic acid and trichloroacetic acid; sulfonic acids such as benzenesulfonic acid, toluenesulfonic acid and methanesulfonic acid.

Among these promoters or auxiliary agents, preferable are alkali metal halide, alkaline earth metal halide, ammonium halide and mineral acid, more preferable are alkali metal halide and ammonium halide, particularly preferable are sodium chloride and ammonium chloride.

The reaction promoter or reaction auxiliary agent is usable for example, in an amount of 0.01 to 10 weight parts, preferably 0.1 to 1 weight part, per weight part of the compound of the formula (1). The reaction promoter or reaction auxiliary agent is used preferably in the form of an aqueous solution having a concentration of more than 0.1%. The reaction proceeds smoothly by use of the reaction promoter or reaction auxiliary agent. Although the reason why the reaction is promoted is not clearly explained, it is considered that the promoter or agent can render an active species derived from aluminum, iron, magnesium or like metal and/or bismuth stable electrochemically.

The reaction is conducted usually at about 0° C. to 100° C., preferably about 10° C. to 50° C., although suitably selected depending on the starting material or solvent, etc. The reaction is conducted usually for about 1 to 24 hours, preferably 3 to 12 hours.

After completion of the reaction, for example, the desired penicillanic acid compound of the formula (2) can be isolated in almost pure state by a usual extraction procedure. When required, recrystallization, column chromatography or like widely used purification means can be applied.

Further, in case of preparing and isolating the monohalogenated penicillanic acid compound of the formula (1b) from the dihalogenated penicillanic acid compound of the formula (1a), the reaction can be terminated after watching the reaction situation by HPLC, thin layer chromatography, NMR, etc., and confirming the amount of monohalogenated product. Usually, a mixture of the monohalogenated penicillanic acid compound of the formula (1b) and the penicillanic acid compound of the formula (2) is obtained. These compounds can be isolated by liquid chromatography or like separating means.

BEST MODE OF CARRYING OUT THE INVENTION

The present invention will be described below in detail with reference to examples to which, however, the invention is not limited.

EXAMPLE 1

A 86.6 g quantity of 6,6-dibromo-2,2-dimethylpenam-3-carboxylic acid 1-oxide diphenylmethyl ester (Compound 1) [compound of the formula (1) wherein X=Y=Br, R=diphenylmethyl, n=1] was dissolved in 300 mL of dichloromethane. To the solution was added 36 mL of methanol with stirring and then added a suspension of 1.05 g of metal bismuth in 112 mL of 20% aqueous solution of sodium chloride. While maintaining at 20 to 25° C., to the mixture was added 10 g of aluminum powder, each 1 g, at intervals of 10 minutes, thereafter the mixture was refluxed with heating. After 23.5 hours, the reaction mixture was cooled to room temperature, an organic layer was separated and washed with diluted hydrochloric acid and 5% aqueous solution of sodium chloride. The organic layer was concentrated to give 2,2-dimethylpenam-3-carboxylic acid 1-oxide diphenylmethyl ester (Compound 2) [compound of the formula (2) wherein R=diphenylmethyl, n=1].

Amount: 50.2 g
Yield: 83.3%

EXAMPLE 2

A 82.6 g quantity of Compound 1 was dissolved in 300 mL of dichloromethane. To the solution was added 115 mL of 20% aqueous solution of ammonium chloride and 36 mL of methanol with stirring. After adding 1.6 g of bismuth chloride, 10 g of aluminum powder was gradually added to the mixture while maintaining at 20 to 30° C. The mixture was reacted for 5 hours while maintaining at 20 to 30° C. After adding 120 mL of water, insoluble metalresidue was filtered and an orgaic layer was separated. The organic layer was washed with 120 mL of 5% aqueous solution of sodium chloride. The organic layer was concentrated to give Compound 2.

Amount: 52.0 g
Yield: 89%

EXAMPLES 3 to 12

The same reaction as in Example 2 were conducted except that ammonium chloride was replaced by a salt or acid listed in Table 1, and bismuth chloride was replaced by a bismuth compound listed in Table 1.

TABLE 1

| Example | bismuth compound | salt or acid | yield |
|---|---|---|---|
| 3 | $BiCl_3$ | NaCl | 91% |
| 4 | $BiCl_3$ | NaBr | 80% |
| 5 | $BiCl_3$ | $CaCl_2$ | 73% |
| 6 | $BiCl_3$ | $MgCl_2$ | 70% |
| 7 | $BiCl_3$ | $(CH_3)_3NHCl$ | 72% |
| 8 | $BiCl_3$ | $H_2SO_4$ | 79% |
| 9 | $Bi_2(SO_4)_3$ | $NH_4Cl$ | 91% |
| 10 | $Bi_2(SO_4)_3$ | NaCl | 90% |
| 11 | $Bi(NO_3)_3 \cdot 5H_2O$ | $NH_4Cl$ | 87% |
| 12 | $Bi(NO_3)_3 \cdot 5H_2O$ | NaCl | 87% |

EXAMPLE 13

The same reaction as in Example 2 were conducted except that, as a solvent, dichloromethane was replaced by ethyl acetate to obtain Compound 2 in a yield of 83%.

EXAMPLE 14

The same reaction as in Example 2 were conducted except that, as a solvent, dichloromethane was replaced by a mixture of dichloromethane and dimethylformamide (volume ratio=100:150) to obtain Compound 2 in a yield of 83.7%.

EXAMPLE 15

The same reaction as in Example 2 were conducted except that methanol was not added to obtain Compound 2 in a yield of 68.4%.

EXAMPLE 16

The same reaction as in Example 2 were conducted except that 6-bromo-2,2-dimethylpenam-3-carboxylic acid 1-oxide diphenylmethyl ester (Compound 3) [compound of the formula (1) wherein X=Br, Y=H, R=diphenylmethyl, n=1] was used in place of Compound 1 to obtain Compound 2 in a yield of 90%.

EXAMPLE 17

A 82.6 g quantity of 6,6-dibromo-2,2-dimethylpenam-3-carboxylic acid 1-oxide p-nitrobenzyl ester (Compound 4) [compound of the formula (1) wherein X=Y=Br, R=p-nitrobenzyl, n=1] was dissolved in 300 mL of dichloromethane. To the solution was added 115 mL of 20% aqueous solution of ammonium chloride and 36 mL of methanol with stirring. After adding 1.6 g of bismuth chloride and 10 g of aluminum powder at one time, the mixture was reacted at 40° C. for 8 hours. An organic layer was separated and concentrated by an evaporator to give 6-bromo-2,2-dimethylpenam-3-carboxylic acid 1-oxide p-nitrobenzyl ester (Compound 5) [compound of the formula (1b) wherein X=Br, Y=H, R=p-nitrobenzyl, n=1] in a yield of 65%.

The obtained Compound 5 (45.4 g) was subjected to the same reaction to give 2,2-dimethylpenam-3-carboxylic acid 1-oxide p-nitrobenzyl ester (Compound 6) [compound of the formula (2) wherein R=p-nitrobenzyl, n=1] in a yield of 85% (from Compound 5).

EXAMPLE 18

A 42 g quantity of Compound 1 was dissolved in 300 mL of dichloromethane. To the solution was added 0.9 g of bismuth sulfate and 57 mL of 20% aqueous solution of sodium chloride with stirring. To the mixture were added 10 g of iron powder and 17 mL of methanol with stirring at room temperature for 9 hours. Further, the mixture was stirred for 10 hours with adding 0.8 g of bismuth sulfate, and stirred at 35° C. for 2 hours. After completion of reaction, 100 mL of water was added and an orgaic layer was separated. The organic layer was washed with 100 mL of 5% aqueous solution of sodium chloride. The organic layer was concentrated to give Compound 2.

Amount: 26.7 g
Yield: 89.9%

EXAMPLE 19

A 20 g quantity of Compound 1 was dissolved in 75 mL of dichloromethane. To the solution was added 0.9 g of bismuth sulfate and 30 mL of 20% aqueous solution of sodium chloride with stirring. To the mixture were added each of 0.5 to 0.6 g of magnesium ribbon at intervals of 30 minutes in total amount of 4 g. The mixture was stirred at room temperature for 10 hours. Water (100 mL) was added and an orgaic layer was separated. The organic layer was washed with 5% aqueous solution of sodium chloride. The organic layer was concentrated and the residue was subjected to column chromatography (toluene:ethyl acetate=5:1) to give Compound 2 and Compound 3, respectively.

Compound 2 Amount: 8.6 g, Yield: 61%
Compound 3 Amount: 2.8 g, Yield: 17%

INDUSTRIAL APPLICABILITY

The penicillanic acid compound obtained by the present process is useful, for example, as an intermediate for β-lactamase inhibitor.

The invention claimed is:
1. A process for preparing a penicillanic acid compound of formula (2) comprising reacting a halogenated penicillanic acid compound of formula (1), (a) in the presence of a metal bismuth or bismuth compound, and at least one reaction promoter, selected from among alkali metal halide, alkaline earth metal halide, ammonium halide, alkyl ammonium salt, mineral acid, organic carboxylic acid and organic sulfonic acid, (b) with a metal having a lower standard oxidation-reduction potential than bismuth to obtain compound (2)

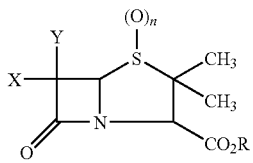
(1)

(X and Y are a hydrogen atom or halogen atom, provided that X and Y are not hydrogen atoms at the same time, n is an integer of 0 to 2, and R is a carboxylic acid protecting group)

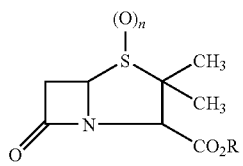
(2)

(n and R are the same as above).

2. A process for preparing a penicillanic acid compound of formula (2)

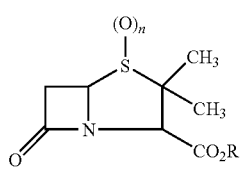
(2)

(n is an integer of 0 to 2, and R is a carboxylic acid protecting group) comprising reacting a dihalogenated penicillanic acid compound of formula (1a), (a) in the presence of a metal bismuth or bismuth compound, and at least one reaction promoter selected from among alkali metal halide, alkaline earth metal halide, ammonium halide, alkyl ammonium salt, mineral acid, organic carboxylic acid and organic sulfonic acid, (b) with a metal having a lower standard oxidation-reduction potential than bismuth to obtain a monohalogenated penicillanic acid compound of formula (1b), and reacting compound (1b) with a metal having a lower standard oxidation-reduction potential than bismuth in the presence of a metal bismuth or bismuth compound, and at least one reaction promoter selected from among alkali metal halide, alkaline earth metal halide, ammonium halide, alkyl ammonium salt, mineral acid, organic carboxylic acid and organic sulfonic acid, to obtain compound (2)

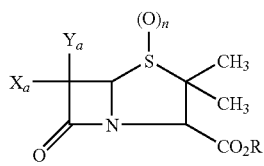
(1a)

($X_a$ and $Y_a$ are halogen atoms, and n and R are the same as above)

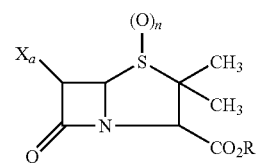
(1b)

($X_a$, n and R are the same as above).

3. A process for preparing a monohalogenated penicillanic acid compound of formula (1b)

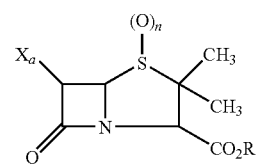
(1b)

($X_a$ is a halogen atom, n is an integer of 0 to 2, and R is a carboxylic acid protecting group)

comprising reacting a dihalogenated penicillanic acid compound of formula (1a),

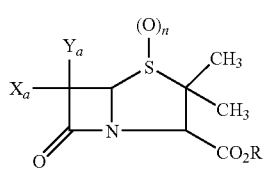
(1a)

($X_a$ and $Y_a$ are halogen atoms, n is an integer of 0 to 2, and R is a carboxylic acid protecting group)
(a) in the presence of a metal bismuth or bismuth compound, and at least one reaction promoter selected from among alkali metal halide, alkaline earth metal halide, ammonium halide, alkyl ammonium salt, mineral acid, organic carboxylic acid and organic sulfonic acid, (b) with a metal having a lower standard oxidation-reduction potential than bismuth to obtain compound (1b).

4. A process for preparing a penicillanic acid compound of formula (2)

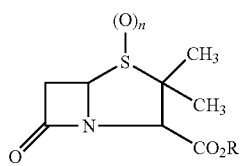

(2)

(n is an integer of 0 to 2, and R is a carboxylic acid protecting group) comprising reacting a monohalogenated penicillanic acid compound of formula (1b),

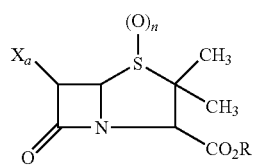

(1b)

(Xa is a halogen atom, n is an integer of 0 to 2, and R is a carboxylic acid protecting group)

(a) in the presence of a metal bismuth or bismuth compound, and at least one reaction promoter selected from among alkali metal halide, alkaline earth metal halide, ammonium halide, alkyl ammonium salt, mineral acid, organic carboxylic acid and organic sulfonic acid, (b) with a metal having a lower standard oxidation-reduction potential than bismuth to obtain compound (2).

5. The process as defined in any of claims 1 to 4 wherein the bismuth compound is bismuth halide, bismuth salt of mineral acid, bismuth oxyhalide, bismuth salt of aliphatic acid or bismuth oxide.

6. The process as defined in any of claims 1 to 4 wherein the metal having a lower standard oxidation-reduction potential than bismuth is one selected from aluminum, iron and magnesium.

7. The process as defined in any of claims 1 to 4 wherein the reaction promoter is at least one selected from alkali metal halide, alkaline earth metal halide, ammonium halide and mineral acid.

8. The process as defined in any of claims 1 to 4 wherein the reaction is conducted in the presence of a solvent.

9. The process as defined in claim 8 wherein the solvent is a hydrocarbon halide.

10. The process as defined in claim 8 wherein the solvent is a mixture of a lower alkyl alcohol and hydrocarbon halide.

11. The process as defined in any of claims 1 to 4 wherein the reaction is conducted in the presence of water.

* * * * *